United States Patent
Bircher et al.

(10) Patent No.: US 7,385,204 B2
(45) Date of Patent: Jun. 10, 2008

(54) FLUID TREATMENT DEVICE

(75) Inventors: Keith Bircher, Toronto (CA); Walter G. Tramposch, Moon Township, PA (US); Mike Matuszewski, Pittsburgh, PA (US); Michael Pietropaoli, Oakdale, PA (US)

(73) Assignee: Calgon Carbon Corporation, Pittsburgh, PA (US)

( * ) Notice: Subject to any disclaimer, the term of this patent is extended or adjusted under 35 U.S.C. 154(b) by 779 days.

(21) Appl. No.: 10/696,072

(22) Filed: Oct. 29, 2003

(65) Prior Publication Data

US 2005/0092932 A1    May 5, 2005

(51) Int. Cl.
 *G01N 21/00* (2006.01)
(52) U.S. Cl. .......................... 250/455.11; 250/453.11; 250/454.11
(58) Field of Classification Search ........... 250/453.11, 250/454.11, 455.11
See application file for complete search history.

(56) References Cited

U.S. PATENT DOCUMENTS

| | | | |
|---|---|---|---|
| 3,476,669 A | 11/1969 | Beckmann et al. | |
| 4,103,167 A | 7/1978 | Ellner | |
| 4,179,616 A | 12/1979 | Coviello et al. | |
| 4,204,956 A | 5/1980 | Flatow | |
| 4,367,410 A | 1/1983 | Wood | |
| 4,471,225 A | 9/1984 | Hillman | |
| 4,503,013 A | 3/1985 | Lowther | |
| 4,661,264 A | 4/1987 | Goudy, Jr. | |
| 4,766,321 A | 8/1988 | Lew et al. | |
| 4,767,932 A | 8/1988 | Ellner | |
| 4,897,246 A | 1/1990 | Peterson | |
| 4,922,114 A | 5/1990 | Boehme | |
| 4,948,980 A | 8/1990 | Wedekamp | |
| 4,959,142 A | 9/1990 | Dempo | |
| 4,990,311 A | 2/1991 | Hirai et al. | |
| 5,124,131 A | 6/1992 | Wekhof | |
| 5,151,174 A | 9/1992 | Wiesmann | |
| 5,178,758 A * | 1/1993 | Hwang ...................... 210/256 |
| 5,200,156 A | 4/1993 | Wedekamp | |
| 5,208,461 A | 5/1993 | Tipton | |
| 5,302,298 A | 4/1994 | Leitzke | |
| 5,397,552 A | 3/1995 | Weigold et al. | |
| 5,503,800 A | 4/1996 | Free | |
| 5,505,912 A | 4/1996 | Hallett | |
| 5,851,399 A | 12/1998 | Leitzke | |
| 5,874,740 A | 2/1999 | Ishiyama | |
| 6,015,229 A | 1/2000 | Cormack et al. | |
| 6,193,938 B1 | 2/2001 | Wedekamp | |

(Continued)

FOREIGN PATENT DOCUMENTS

DE    43 05 227 C1    8/1994

(Continued)

*Primary Examiner*—David A. Vanore
(74) *Attorney, Agent, or Firm*—Cohen & Grigsby, P.C.

(57) ABSTRACT

The inventive system comprises a housing for receiving a flow of fluid. The invention for the first time uses a modular assembly of UV lamps. The modular assembly comprises at least two UV sources substantially parallel to each other and transverse to said flow. In an embodiment, one of the UV sources is disposed in a plane below all such other lamps and adapted to be run at a power higher than that of all such other lamps. The inventive arrangement is combined with a baffle arrangement wherein the baffles are preferably positioned in such a way to direct the fluid flow into the treatment area.

17 Claims, 8 Drawing Sheets

U.S. PATENT DOCUMENTS

| | | |
|---|---|---|
| 6,224,759 B1 | 5/2001 | Whitby et al. |
| 6,264,888 B1 | 7/2001 | Palestro et al. |
| 6,313,468 B1 | 11/2001 | Wedekamp |
| 6,342,128 B1 | 1/2002 | Tabatabaie-Raissi et al. |
| 6,500,312 B2 | 12/2002 | Wedekamp |
| 6,500,346 B1 | 12/2002 | Taghipour et al. |
| 6,500,387 B1 | 12/2002 | Bigelow |
| 6,940,075 B2 | 9/2005 | Schulz |
| 7,038,219 B2 * | 5/2006 | Clark et al. ............ 250/455.11 |
| 2001/0031229 A1 | 10/2001 | Spjut et al. |
| 2002/0033369 A1 | 3/2002 | Bender |
| 2003/0129105 A1 | 7/2003 | Boehme |

FOREIGN PATENT DOCUMENTS

| | | |
|---|---|---|
| EP | 0 317 735 | 9/1988 |
| GB | 1 584 385 | 6/1977 |
| JP | 01007988 A | 1/1989 |
| JP | 01007989 A | 1/1989 |
| JP | 01176488 A | 7/1989 |
| JP | 01176489 A | 7/1989 |
| JP | 01176490 A | 7/1989 |
| JP | 2001029941 A | 2/2001 |
| JP | 2001212214 A | 8/2001 |
| WO | WO 93/15830 | 8/1993 |

* cited by examiner

FLUID TREATMENT DEVICE

FIELD OF THE INVENTION

The present invention relates to an apparatus for treating fluids with ultraviolet ("UV") light, and in particular provides an apparatus that equally distributes UV dose so as to achieve increased treatment effectiveness.

BACKGROUND OF THE INVENTION

The use of UV radiation to kill microorganisms in air or in fluid systems is well known. Often such systems comprise UV reactors that have rows of UV lamps. It is known to offset successive rows so that the fluid passes through the spaces between the lamps in the first row and contacts the lamps in the second row. A patent to Wedekamp, U.S. Pat. No. 5,200,156, ("Wedekamp") discloses one such system. The primary concern disclosed in Wedekamp was offsetting the lamps so that the light can pass upstream and downstream unobstructed.

However, the system disclosed in Wedekamp and other traditional UV systems have failed to provide a apparatus that is able to equally distribute UV dose throughout the system, and that is therefore capable of achieving uniformity in dose. The failure of those traditional systems relates to a phenomenon that has been, up until now, ignored. That phenomenon is that the UV lamps that are used to treat fluids emit less UV in the downward direction than in the upward direction. This is particularly relevant with large medium pressure mercury arc lamps. Therefore, in traditional systems wherein the UV light sources are arranged next to one another and sometimes in offset rows, there could be areas in the reactor where the dose is low. This is especially so in the area below the lamps, where, as described above, the lamp output is reduced, thereby contributing to a low dose in this zone and hence a wide dose distribution. Therefore, a traditional system may provide some of the fluid with a low dose of UV and some of the fluid with a high dose. Ideally, UV treatment systems and methods would provide a narrow dose distribution.

It would therefore be desirable to eliminate the undesirable effect of a non-uniform dose distribution. It would further be desirable to increase uniformity in dose distribution by causing more of the fluid to flow into the treatment area.

Another problem in designing UV reactors for treatment of fluids is that in an installed system, the fluid quality and flow rate may vary from one system to another and from moment to moment. Thus, there is a need for modular assemblies that can be incorporated into a reactor in any number to account for such variations.

SUMMARY AND OBJECT OF THE INVENTION

The present invention is a novel fluid treatment device that for the first time takes into account the phenomenon described above wherein UV sources emit less UV light in the downward direction than in the upward direction. The inventive system comprises a housing for receiving a flow of fluid. The invention for the first time uses a modular assembly of UV lamps. The modular assembly comprises at least two UV sources substantially parallel to each other and transverse to said flow. In an embodiment, one of the UV sources is disposed in a plane below all such other lamps and adapted to be run at a power higher than that of all such other lamps. The inventive arrangement is combined with a baffle arrangement wherein the baffles are preferably positioned in such a way to direct the fluid flow into the treatment area.

In this way, the invention achieves its objects. One of the objects of the invention is to provide a UV light arrangement wherein the lower lamp is run at a higher power so as to provide a uniform dose of UV light being emitted across the cross-section of the reactor, thereby achieving a uniform dose distribution.

It is a further object of the present invention to provide an arrangement of baffles that causes the fluid to flow in close proximity to the UV sources, thereby increasing dose effectiveness.

It is still a further object of the invention to provide a geometry for an arrangement of baffles that increases uniformity in dose distribution by causing the fluid to flow into an area uniformly treated by the UV sources by adjusting the dimensions of the lower baffles.

It is still a further object of the current invention to provide the fluid treatment zones in modules that can be incorporated in a reactor in any number sufficient to achieve the required dose. For example, for a given flow if the water quality is low (low percent transmitence for a UV reactor) more modules can be included to achieve the required treatment dose. In addition, for a given reactor, during operation, if the flow rate through the reactor is low or the water quality is high, not all the modules need be operated thereby reducing the cost of operating the reactor. This high degree of "turndown" in the reactor is attractive both in sizing the reactor for a given application and in operating the reactor to reduce operating cost.

Still further, an object of the present invention is to incorporate assembly modules that are substantially tuned to a corresponding set of lamps and baffles such that they can be run independently of other modules and such that any number and position of modules can be run in combination to achieve the required dose.

DETAILED DESCRIPTION OF THE PRESENTLY PREFERRED EMBODIMENTS

Figure 1:
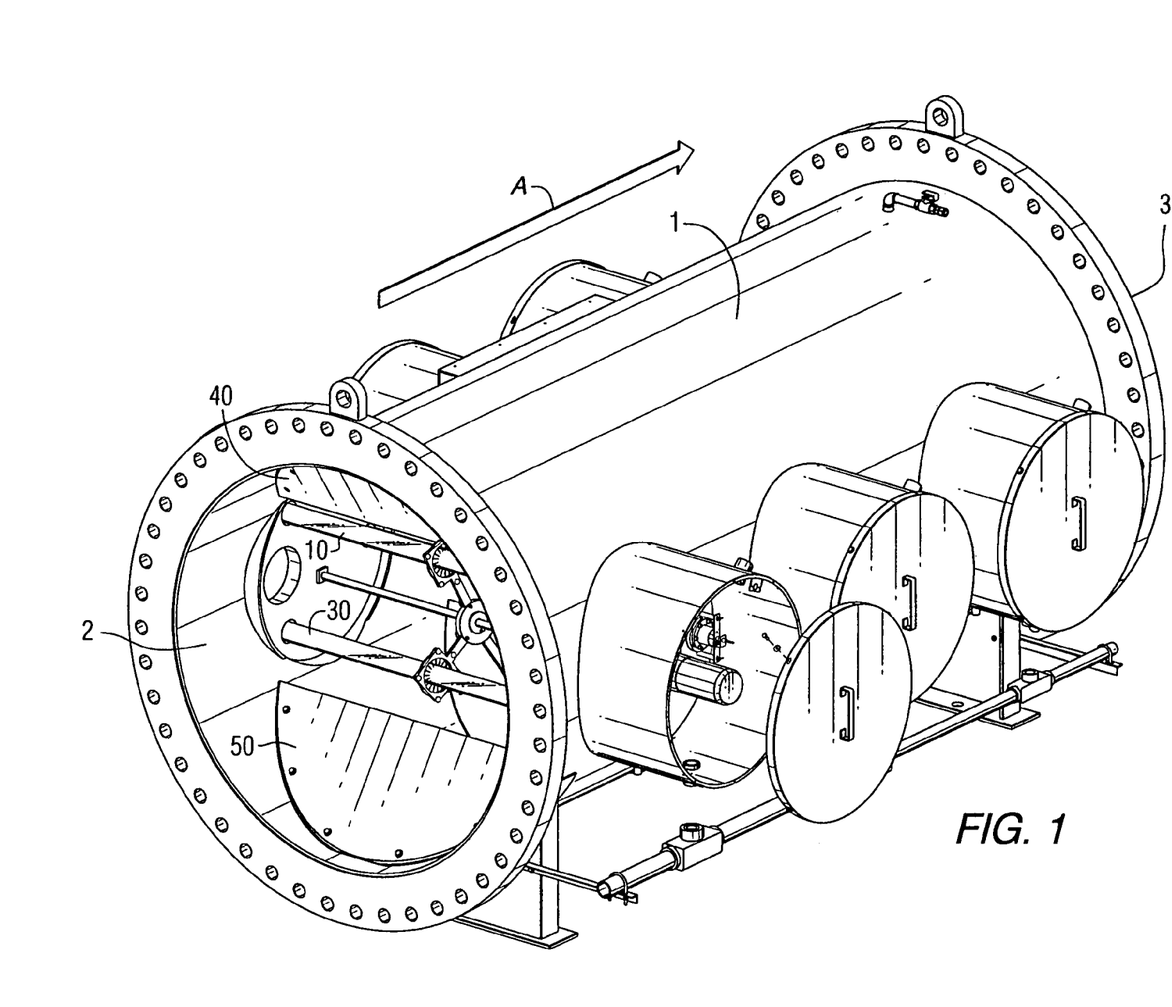
FIG. 1 is on isometric view of a reactor having the inventive system therein.
Figure 2:
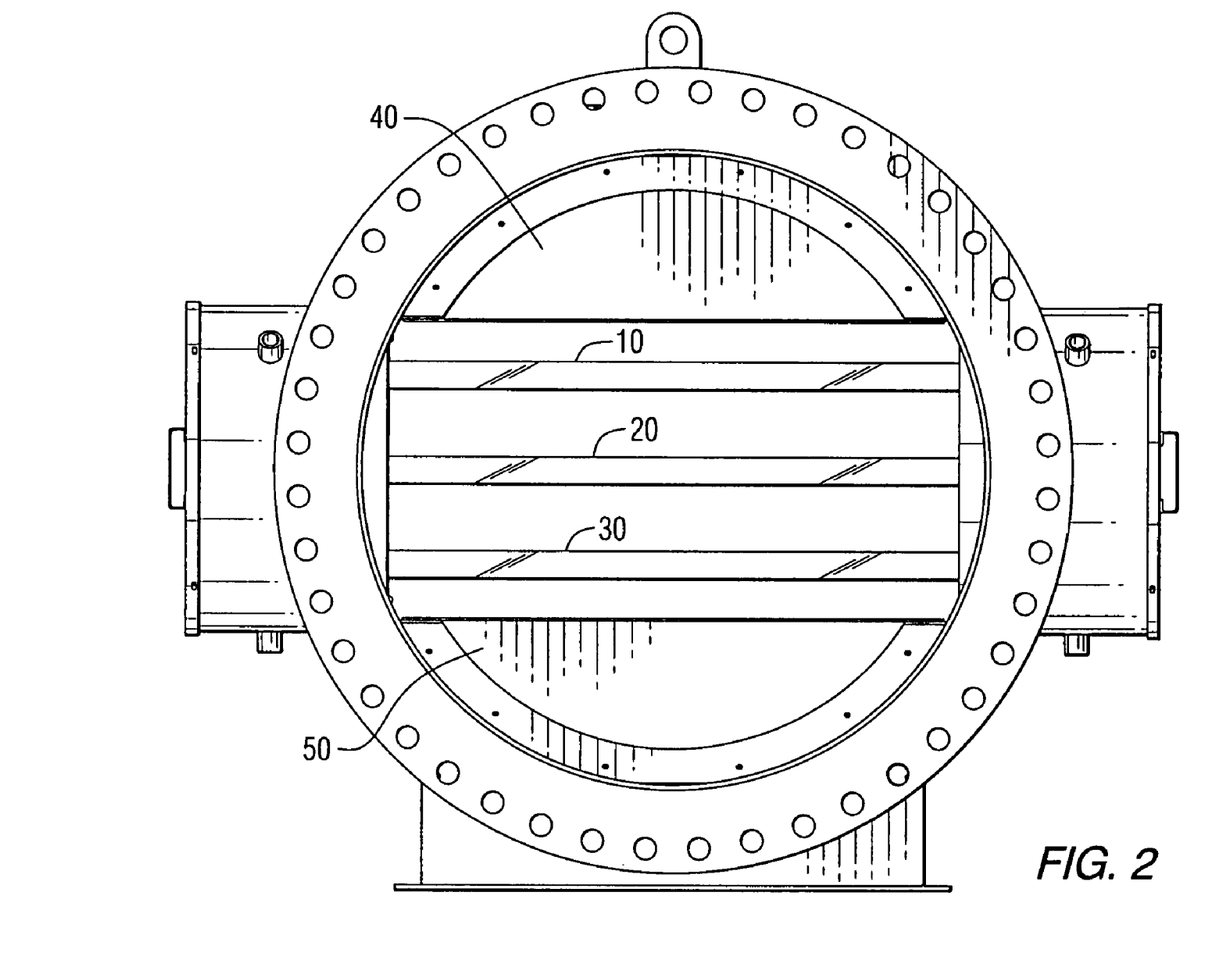
FIG. 2 is a side view of the reactor.

FIG. 1 shows a fluid treatment device according to the present invention. The fluid treatment device comprises a housing 1 that receives a flow of fluid. The direction of the flow is indicated by arrow A. The housing comprises a fluid inlet 2 into which the fluid flows and a fluid outlet 3 out of which the treated fluid flows. Disposed between the fluid inlet 2 and the fluid outlet 3 is at least one assembly 4, preferably a modular assembly, of UV sources 10,20, and 30.

Figure 3:
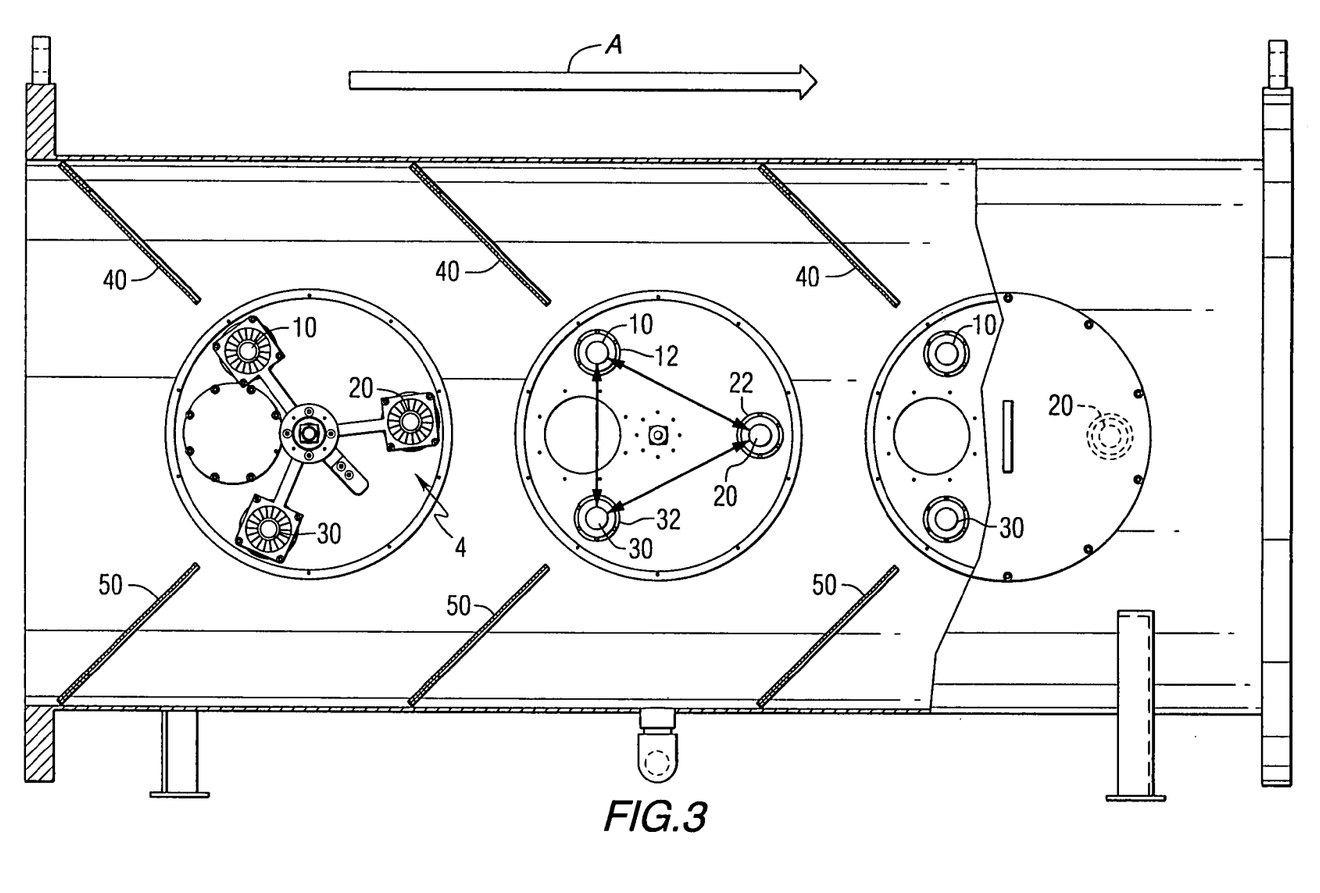
FIG. 3 is a cross sectional view of the reactor.

In FIG. 3, the modular assembly 4 of UV sources 10,20, and 30 comprises at least two UV sources, and in the preferred embodiment contains three UV sources. The UV sources 10,20, and 30 in the assembly are preferably medium pressure UV lamps. Each lamp is contained within a quartz sleeve 12,22, and 32, which are only depicted in FIG. 3 as being in the middle modular assembly, but which are preferably around each lamp. In a preferred embodiment, two lamps or UV sources 10 and 30 are disposed nearer to the inlet 2 (inlet shown in FIG. 1) than the third lamp 20. The UV sources 10 and 30 are spaced apart in the reactor sufficiently far such that the velocity of fluid between them is not high enough to achieve excessive pressure drop in the reactor but sufficiently close such that the UV fluence is not too low to achieve the adequate dose for fluid at the point furthest from the lamps. The third lamp 20 is placed at a position downstream of the first two lamps, 10 and 30, usually at a distance from the first two lamps, 10 and 30, of between 0.25 and 2 times the lamp spacing between the first two lamps 10 and 30. This positioning of the third lamp 20 downstream from the first two, 10 and 30, permits the fluid to flow in an unimpeded fashion between the first two, 10 and 30, but not so far as to allow the fluid that passes furthest from the lamps to wander far away from the third lamp 20, which would cause the fluid to not receive a sufficient dose. Therefore, the angle from the vertical line between the first two, 10 and 30, lamps to the third lamp 20 can be roughly from 45 degrees to 76 degrees. These angles and distances at which the lamps and respective sleeves are disposed to one another is the lamp geometry.

Figure 4:
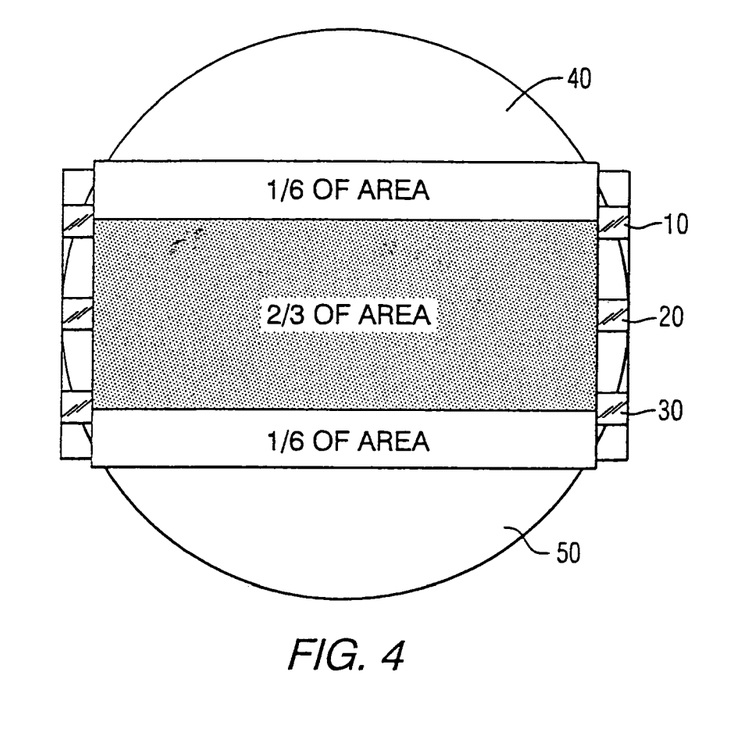
FIG. 4 is a schematic representation of UV distribution in the reactor.
Figure 5:
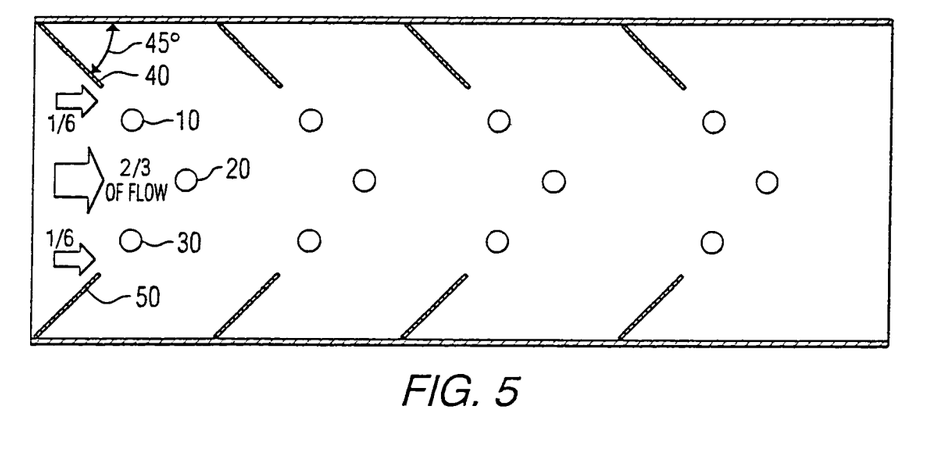
FIG. 5 is a schematic representation of the fluid flow in the reactor.

Each modular assembly has associated with it at least one baffle, preferably a set of baffles, and more preferably a set of two baffles. The preferred arrangement of baffles, 40 and 50, is depicted in FIGS. 3 and 5. The lamp geometry and baffles act as a baffling mechanism to direct the flow of fluid so as to increases uniformity in dose distribution by causing the fluid to flow into an area where it will receive uniform treatment. This is achieved because the geometry and dimension of the baffles are adapted to direct a sufficient amount of fluid between the lamps 10 and 30 and to prevent too much of the water to from passing above lamp 10 or below lamp 30. Typically, the lamp disposed nearest to the top of the housing 10 shines half its UV light down into the middle zone between lamps 10 and 30. The bottom lamp shines half its light up into the middle zone. And the third lamp 20 shines all its light into this middle zone. Thus, as depicted in FIG. 4, two thirds of the UV light is concentrated in this middle zone. Because of this phenomenon, the baffles are arranged such that two thirds of the fluid is directed into this middle zone. Since the flow of fluid is roughly proportional to the area afforded for it to flow, the baffle is sized such that the area for flow is roughly one sixth above the top lamp 10, two thirds between the front lamps 10 and 30 and one sixth below the bottom lamps 30 as shown in FIG. 5.

In a UV reactor baffle height is adjusted from this rough dimension as a result of computer modeling or testing the reactor with different baffle heights and thereby finding an optimum baffle height that produces the best dose distribution while not producing too high a velocity and hence pressure drop through the reactor. In addition the baffles can be positioned upstream of the front lamps and angled towards the lamps. The angling of the baffles helps reduce pressure drop through the reactor while not affecting dose distribution significantly. Pointing the baffle directly at the lamp helps reduce "shadowing" in areas in the reactor behind the baffle. While the baffles in FIGS. 3 and 5 show the baffle at a 45 degree angle and point directly at the lamp, this is not necessary. Baffle angles from 90 degrees to 20 degrees provide similar dose distribution, but provide increasingly lower pressure drop. 45 degrees is shown as a preferred embodiment of the current invention as providing reduced pressure drop without taking up excessive space longitudinally in the reactor.

The baffles can be at any angle to the wall with a smaller angle resulting in lower pressure drop and a larger angle resulting in a shorter length of pipe needed to accommodate the baffle. The baffles are generally disposed upstream of the first pair of lamps to ensure all the water is diverted into the high irradiation zone surrounding the lamp.

Figure 6:
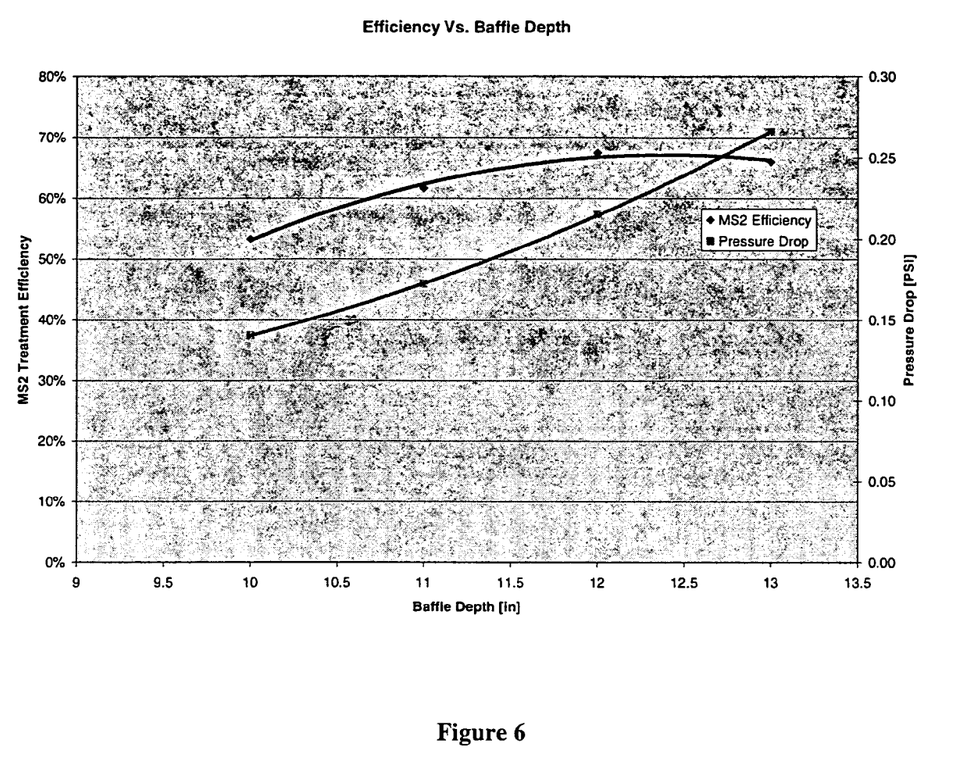
FIG. 6 is a graph showing efficiency versus baffle depth.

The extent to which the baffle penetrates into the reactor and diverts flow from the regions above and below the lamps to the zone between the lamps was determined by computerized modeling of the reactor using a combination of Computational Fluid Dynamics (CFD) and Irradiance Distribution Modeling. The efficiency of a configuration is defined as the ratio of the dose a surrogate organism is subjected to the theorectial dose that would be achieved in a perfectly mixed reactor. This is shown in FIG. 6 together with the pressure drop across the reactor. As would be expected the pressure drop increases with increasing baffle depth. However the efficiency achieves a maximum and reduces as more water is forced between the lamps, wasting some of the UV light above and below the lamps.

At least one of the lamps 30 and its respective sleeve, is disposed in a plane below that of the other lamps 10 and 20 in the assembly. This lamp 30 is run at higher power than the other lamps. This is to address the phenomenon of UV lamps emitting less UV in the downward direction than in the upward direction. By running the lower lamp 30 at a higher power, the fluid at the lower end of the housing will receive the same dose as the fluid that is closer to the lamps, thus providing a uniform distribution of dose. The ratio of power between the lower lamp and the other lamps in each bank varies depending on the lamp length, lamp diameter and lamp power. For long and powerful lamps, the ratio can be up to 1.3 when the lamp is running at full power and up to 2.0 when the lamp is running at reduced power (maximum turndown).

Figure 7:
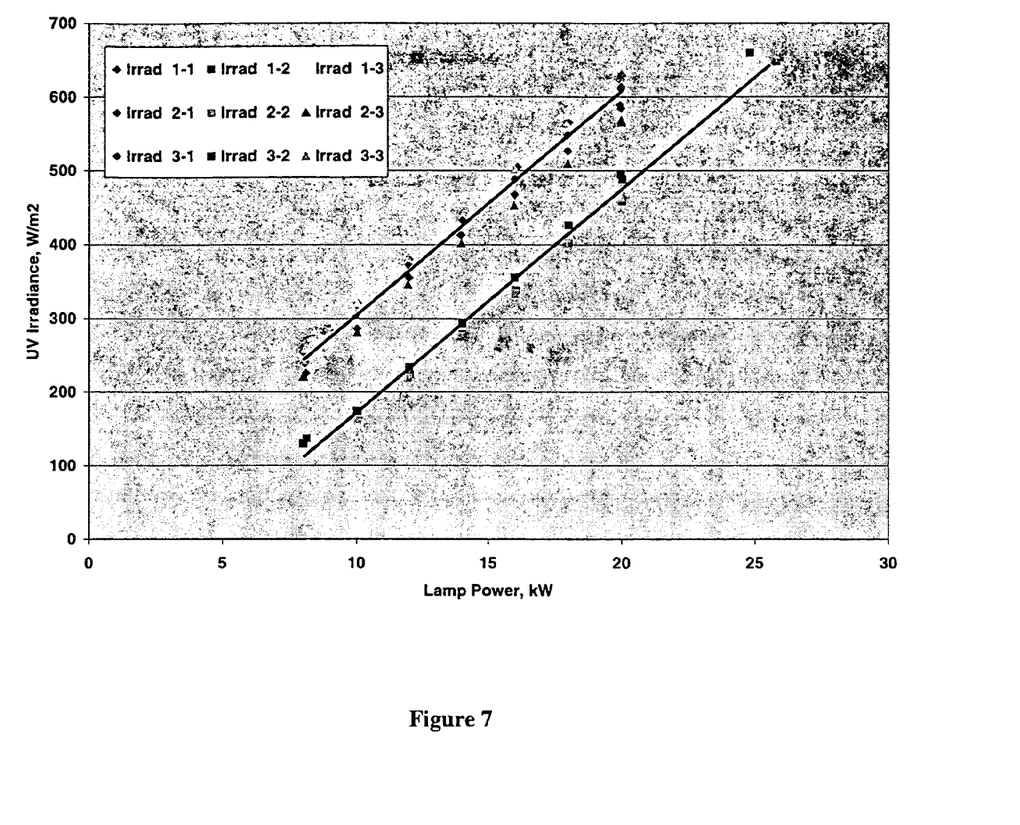
FIG. 7 is showing the relationship between the power of the lowermost UV source and the other UV sources in the according to the present invention.

This relationship between the power of the bottom lamp and the other lamps is shown in FIG. 7 in an operating system where the lower lamps must be powered at approximately 5 kW higher than the upper lamp to get the same UV irradiance of the desired wave length. Field data from a test reactor showing the relationship between UV Irradiance and Lamp Power. Lamps 1-1, 2-1, 3-1, 1-3, 2-3 and 3-3 are viewed with the UV Sensor from above. Lamps 1-2, 2-2 and 3-2 are viewed from below at the same distance from the lamp. This shows that approximately 5 kW more power is needed to achieve the same irradiance below the lamp as above the lamp.

Alternatively, the baffles of the fluid treatment device are arranged so that at least one baffle is adapted to direct flow of fluid such that about one-quarter of the fluid flows above a top of one UV source, one quarter of the fluid flows below the bottom of the UV source and half of the fluid flows between the UV sources.

This power premium, as high as 20% of full lamp power in the example above, varies depending on the lamp power, lamp dimensions and lamp environment. In lower powered and correspondingly shorter lamps, it is much less pronounced.

Figure 8:
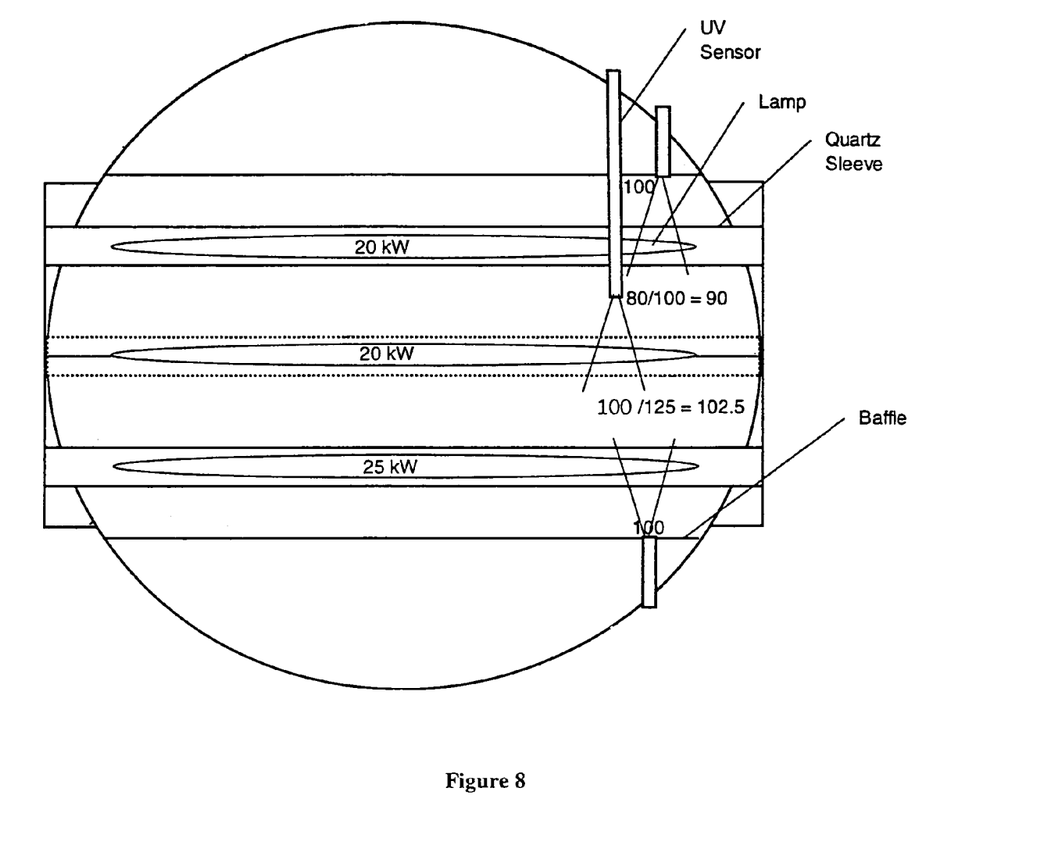
FIG. 8 is a schematic representation how the claimed invention achieves a uniform dose distribution in light the newly-discovered phenomenon disclosed herein.

To compensate for this phenomenon and achieve an even dose distribution in a reactor the bottom lamp can be run at higher power than the upper lamps. This is illustrated in the FIG. 8 where, for example, operating the upper two lamps at 20 kW produces an irradiance of 100 above and 80 below. Operating the bottom lamp at 25 kW produces an Irradiance of 125 above and 100 below. The most vulnerable parts of the reactor are the points furthest from the lamps where the irradiance is lowest but between the baffles where the flow velocity is high. In the example the combined irradiance is 100 at the top baffle, 90 between the top lamp and middle lamp, 102.5 between the middle lamp and bottom lamp and 100 at the bottom baffle. Thus, the irradiance distribution has been evened out by running the lower lamp at higher power thus improving the overall efficiency of the reactor. This can be simply achieved by running the each of the lamps to achieve the same UV setpoint value (100 in this case) and applying the UV irradiance sensor such that upper UV sources are viewed from above and the lowermost from below.

Figure 9:
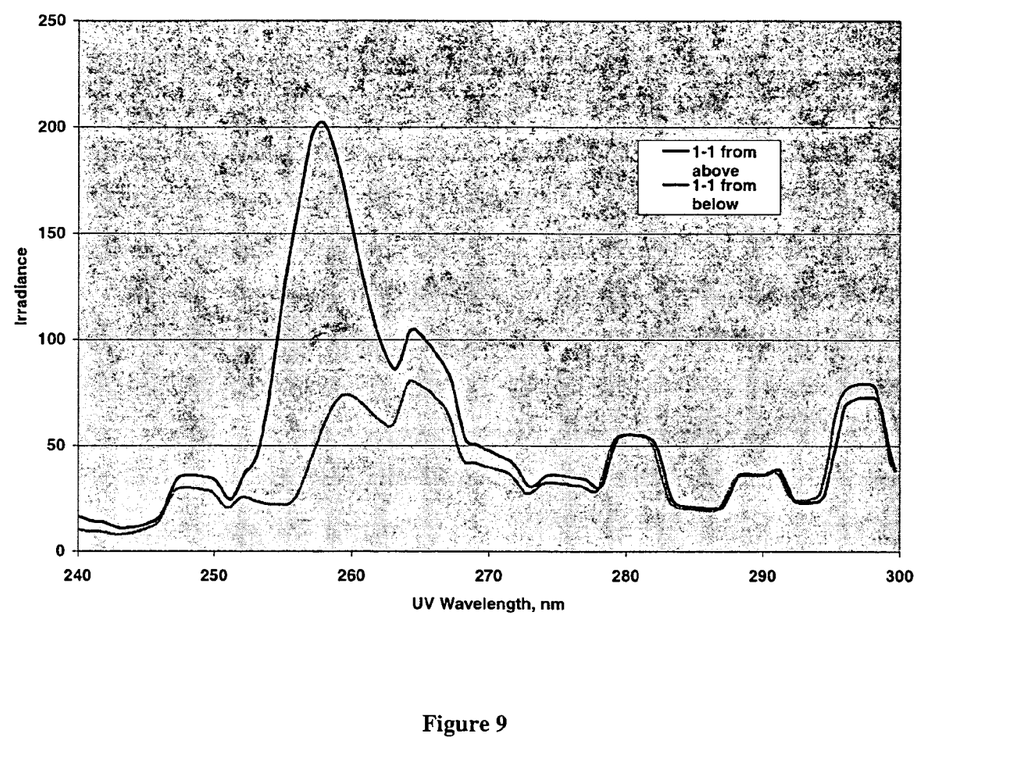
FIG. 9 is a graph showing thermal convection effects above and below UV sources of the present invention.

It has also been surprisingly found that because of thermal convection effects surrounding and within the lamp, the plasma arc tends to rise up in the lamp. This leaves an area below the lamp where mercury vapor is present but no plasma exists and hence, no emission of UV light. This mercury vapor will absorb UV, in particular in the wavelength band around 254 nm were mercury absorption is the strongest. The dramatic drop in the desired UV measured by a spectroradiometer between 252 nm and 260 nm is shown in FIG. 9, which involves Spectral Irradiance measured above and below a lamp and shows the reduction in the output in the band around 254 nm.

This effect is also dependent on the dimensions and other design parameters of the lamp. A longer lamp or a lamp with a larger diameter will show a more accentuated drop in output in this region as illustrated. A shorter lamp or thinner lamp will reduce this effect. It is therefore important to choose a lamp for service in the reactors described here to minimize this effect. For higher-powered lamps, however, it is not possible to eliminate the effect altogether.

An alternative method of dealing with the lower irradiance in the bottom of the reactor due to the lower output below the lamps than above, is to increase the length or alter the positioning of the lower baffle 50 (shown in FIGS. 3 and 5) in order to reduce the flow of fluid into this zone of lower irradiance. Another alternative to running the bottom lamp at a higher power is to move the lower lamp closer to the bottom of the reactor at a distance from other lamps such that a uniform irradiance is achieved.

While presently preferred embodiments of the invention have been shown and described, the invention may be otherwise within the scope of the appended claims.

What is claimed is:

1. A fluid treatment device comprising:
   a. a housing for receiving a flow of fluid, said housing comprising a fluid inlet and a fluid outlet; and
   b. at least one assembly of UV sources between said fluid inlet and said fluid outlet, said assembly comprising at least two UV sources horizontally disposed in a substantially vertical plane transverse to the flow of fluid, at least one of said at least two UV sources being disposed in said plane below such other UV sources as a bottommost UV source, and at least one of said at least two UV sources being disposed in said plane above such other UV sources as an uppermost UV source, said bottommost UV source operating at the same or a higher power level than that of all such other UV sources in said assembly such that said fluid flowing below said bottommost UV source receives a UV irradiance that is at least substantially equal to a UV irradiance received by said fluid flowing above said uppermost UV source.

2. The fluid treatment device according to claim 1 wherein a ratio of the power of said bottommost UV source to that of all other UV sources is from about 1.0 to 2.0.

3. A fluid treatment device according to claim 1 wherein a first UV Sensor is positioned at a top of each of said at least one assemblies pointing down at and measuring a UV irradiance from said uppermost UV source and a second UV Sensor is positioned at a bottom of each of said at least one assemblies pointing up at and measuring a UV irradiance from said bottommost UV source.

4. A fluid treatment device according to claim 3 wherein said measured UV irradiance is used to control a power of said UV sources in each of said at least one assemblies such that said UV irradiance received by said UV fluid flowing below said bottommost UV source is at least substantially equal to said UV irradiance received by said fluid flowing above said uppermost UV source.

5. The fluid treatment device according to claim 1, wherein each said assembly corresponds to at least one baffle, said at least one baffle operating to direct said flow of fluid into an area of each said assembly such that said fluid passes within a certain maximum distance from at lease one of said UV sources.

6. The fluid treatment device according to claim 5 having two said UV sources in each said at least one assembly wherein said at least one baffle is adapted to direct said flow of fluid such that about ¼ of said fluid flows above said uppermost UV source, about ¼ of said fluid flows below said bottommost UV source and about ½ of said fluid flows between said uppermost and said bottommost one UV sources.

7. The fluid treatment device according to claim 5 wherein at least one baffle is arranged to bisect at least one UV source on a parallel axis.

8. A method of operating a fluid treatment device according to claims 1 or 5 wherein each said at least one assembly is operable independent of said each other at least one assemblies.

9. A fluid treatment device according to claim 8 wherein two UV sources are positioned in said substantially vertical plane followed by a third UV source positioned downstream from a midpoint in said vertical plane between said other two UV sources at a distance between about 0.25 and 2 times the distance between said other two UV sources.

10. A fluid treatment device according to claim 9 wherein said at least one baffle is adapted to direct said flow of fluid such that about ⅙ of said fluid flows above an uppermost UV source, about ⅙ of said fluid flows below said bottommost UV source and about ⅔ of said fluid flows between said uppermost and bottommost UV sources.

11. The fluid treatment device according to claim 1 or 5 wherein two UV sources are positioned in said substantially vertical plane followed by a third UV source positioned downstream from a midpoint in said vertical plane between said other two UV sources at a distance between about 0.25 and 2 times the distance between said other two UV sources.

12. The fluid treatment device according to claim 11 wherein said at least one baffle is adapted to direct said flow of fluid such that about ⅙ of said fluid flows above an uppermost UV source, about ⅙ of said fluid flows below said bottommost UV source and about ⅔ of said fluid flows between said uppermost and bottommost UV sources.

13. The fluid treatment device of claim 11 wherein the third UV source is positioned at an angle of about 45 to 76 degrees from the vertical plane.

14. The fluid treatment device comprising:
 a) a housing for receiving a flow of fluid, said housing comprising a fluid inlet and a fluid outlet;
 b) at least one assembly of UV sources disposed between said fluid inlet and said fluid outlet, each said assembly comprising at least one UV source, said at least one UV source being horizontally disposed traverse to the flow of fluid; and
 c) a lower and an upper baffle wherein said lower baffle is longer than said upper baffle such that said fluid flowing below the bottommost of said at least one UV source receives a UV irradiance that is at least substantially equal to a UV irradiance received by said fluid flowing above said uppermost of said UV sources.

15. A fluid treatment device according to claims 5 or 14 wherein said at least one baffle is disposed at an angle of between about 90 degrees to 20 degrees to a top and bottom wall of said fluid treatment device.

16. The fluid treatment device of claim 14 wherein said at least one assembly of UV sources comprises at least two UV sources.

17. A fluid treatment device comprising:
 a) a housing for receiving a flow of fluid, said housing comprising a fluid inlet and a fluid outlet; and
 b) at least one assembly of UV sources disposed between said fluid inlet and said fluid outlet, each said assembly comprising at least one UV source disposed between said fluid inlet and said fluid outlet, said at least one UV source being horizontally disposed traverse to the flow of fluid, wherein a bottommost of said at least one UV source is positioned relatively closer to a bottom of said fluid treatment device than an uppermost of said at least one UV source is to a top of said fluid treatment device.

* * * * *